United States Patent [19]
Heasley

[11] Patent Number: 5,800,173
[45] Date of Patent: Sep. 1, 1998

[54] ABSORBENT POLYMER ROLL HOLDER

[76] Inventor: John M. Heasley, 922 Benton Dr., Iowa City, Iowa 52246

[21] Appl. No.: 514,108

[22] Filed: Aug. 11, 1995

[51] Int. Cl.⁶ ..................................................... A61C 5/14
[52] U.S. Cl. ........................ 433/138; 433/136; 433/139; 433/94
[58] Field of Search .................... 433/93, 94, 136, 433/138, 139, 140

[56] References Cited

U.S. PATENT DOCUMENTS

| | | | |
|---|---|---|---|
| 1,742,080 | 12/1929 | Jones | 433/136 X |
| 2,507,938 | 5/1950 | Smith | 433/94 |
| 2,714,252 | 8/1955 | Tofflemire | 433/94 |
| 2,791,030 | 5/1957 | Tofflemire | 433/138 X |
| 2,844,873 | 7/1958 | Bober | 433/94 |

*Primary Examiner*—Nicholas D. Lucchesi
*Attorney, Agent, or Firm*—Kent A. Herink; Brian J. Laurenzo; Michael C. Gilchrist

[57] ABSTRACT

An adjustable dental appliance for positioning and retaining absorbent polymer rolls in the oral cavity; in an anatomical location in the mandible (lower jaw) where the submandibular and sublingual glands secrete saliva that interferes with visibility during treatment and contaminates the application of moisture sensitive dental materials. The appliance consists of an adjustable dental device which engages the opposite convex surfaces of a tooth with a clasps joined to clasp arms which are mounted on a resilient transverse member. The relative displacement of the clasp arms are adjusted with a plier-like instrument that separates the clasp arms by stressing the tension of the transverse resilient member until the appliance is in place in relation to a tooth to be engaged. Adjacent to each clasp arm, a rectangular projection of metal and small diameter metal shaft, end free and unsupported to receive two absorptive polymer rolls. One type of roll designed with a locking mechanism engages a spherical enlargement on the metal shaft with plastic members that spread open to accommodate the spherical enlargement and then snap back into place when the metal sphere is engaged. An alternative polymer roll, without a locking mechanism is designed as a cost-effective alternative. Both polymer rolls have as their active ingredient a starch graft copolymer product derived from corn starch and acrylonitrile, by the United States Department of Agricultural Research, the technical name for which is starch-g-poly (starch-co-potassium acrylate).

11 Claims, 7 Drawing Sheets

Starch polymer structure showing grafting at C2 (grafting at C3 position is also possible.)

ABSORBENT POLYMER ROLL HOLDER

BACKGROUND OF THE INVENTION

This instrument series relates generally to dental appliances, and more particularly to dental instruments and products used for the purpose of isolating portions of the oral cavity and maintaining a dry field.

A continuing problem in the practice of dentistry is the contamination of the dental work site by fluids originating within or outside of the oral cavity. That is; (1) the patient's saliva, or (2) blood derived from various procedures, and (3) water sprayed intermittently by dental instruments such as handpieces and air-water syringes. Saliva in particular is continuously present in the oral cavity and contacts all surfaces; the teeth, gingival tissues, tongue, cheeks, palate, etc. Most dental procedures require a dry field of one degree or the other, depending on the nature of the procedure and the type of materials used for restorative purposes. Lack of control of saliva and other fluids during procedures interfere with the quality and performance of dental treatment.

A number of devices are known and used in the art to prevent or limit the likelihood of such distractions. The means most widely used is a rubber membrane, known as the rubber dam, which is anchored directly to teeth that are to be included in a dental procedure. Teeth are isolated from the rest of the oral cavity by being projected through perforations in the rubber membrane so that they are exposed on the side of the rubber dam facing externally of the oral cavity. The rubber dam is positioned such that the tongue and saliva associated with the oral cavity cannot contact the teeth that are then isolated for the procedure. Rubber dams are generally effective at isolating the field from the rest of the oral cavity, but are not used in all procedures due to limitations in the technique, time delays and difficulties in placement of the dam, and varying degrees of need for fluid control with different procedures. Time constraints often force the dental practitioner or hygienist to use more efficient devices to isolate various portions of the oral cavity and maintain a dry field. Various types of oral and periodontal surgery do not require a rubber dam but do require retraction and fluid control for visibility. Prosthetic procedures in particular are generally performed without a rubber dam. Generally, implant procedures, both the surgical phase and the various intricate prosthetic phases that follow are performed without a rubber dam. All hygiene procedures are universally performed without the placement of a rubber dam.

The major dental apparatus that has been used widely by dental practitioners in the past as an alternative to the rubber dam is a cotton roll holder that preceeded the development of the rubber dam and has survived for thirty years along side this device. The survival of this dental device after the development of the rubber dam is an indication that an alternative to the full use of the rubber dam is needed for variations of efficiency and procedure. The device that exists was developed by a dentist over sixty years ago. It is a crude mechanism that relies on the lower external border of the chin for its anchorage within the oral cavity, thus pinching the lip and cheek. It accomodates two cotton rolls, but obscures much of the site that is to be worked on. The patent on the device has expired decades ago, but it continues to be manufactured by a couple of different firms because there is a continuing market for an alternative product. The deficiencies that are inherent in its design limit the scope of its usefulness and desirability in modern dental practice and invite its retirement by a new standard of the state-of-the-art.

A number of other devices exist which function in one capacity or another as saliva ejectors, mouth props with aspirating capacities, and as supporting apparatus for rubber dams. Each has deficiencies, however, that limit the scope of their use and effectiveness as supplementary adjuncts to dentists' needs. None has 'hit the mark' so-to-speak, and established itself as an improvement to the needs of practicing dentists that is universally accepted.

SUMMARY OF THE INVENTION

The invention consists of an absorbent roll holder that is a dental appliance designed for use in all areas of the oral cavity. It attaches to the visible portion of the crown of a tooth by means of reciprocal clasps mounted on clasp arms which engage the opposite convex surfaces of a tooth and are held in place by the reciprocal tension of a resilient transverse metal member. The relative displacement of the clasp arms can be adjusted by engaging the lumen on each clasp arm with a standard dental forceps which is a plier-like instrument that separates the two clasp arms by stressing the tension of the transverse metal member until the appliance is in its proper width in relation to a tooth to be engaged. The forceps is then released and the clasp arms engage the tooth with a reciprocal force sufficient to retain the dental appliance in a fixed position.

Anterior to each clasp arm, the dental appliance contains a forward projection of rectangular metal adjacent to each clasp arm that forms a member that defines the limit of displacement of a cylindrical absorbent roll in an upward direction. Both rectangular metal projections proceed forward from their respective clasp arms in a parallel manner to each other and both are perpendicular to the resilient transverse member. Each rectangular projection contains below it a narrow diameter metal shaft with an enlarged spherical section immediately below and adjacent to the clasp arms. This cylindrical shaft proceeds down and forward from the back end of the absorbent roll holder below the rectangular arm and continues forward in a concentric and parallel manner until it ends below the forward end of the rectangular projection. The forward end of the shaft is free and unsupported so that the end of a cylindrical absorbent roll can be placed on the shaft and pushed backwards until it engages the spherical enlargement of the shaft below the clasp arm and is locked in place by an elastic deformation of three plastic members of the locking mechanism. In addition, the free ends of the two metal shafts that engage the absorbent rolls have a conical tip so that an alternative polymer roll with or without a locking mechansim could be substituted routinely by a dentist by piercing either type of absorbent roll with the small diameter metal shaft and sliding the roll along the cylindrical shaft within it its entire length by simple finger pressure. This feature of the design would allow a dentist to control costs if so desired and if the situation warranted. When the appliance is fixed in place by engaging a tooth with its reciprocal clasps and the absorbent rolls are fixed in place on each shaft, the dental appliance holds the absorbent rolls in a position parallel to and adjacent to the teeth to be worked on. In addition, the design of the appliance positions the absorbent rolls so that that the polymer or absorptive material is in close approximation to the orifices in the oral cavity where the submandibular, sublingual, and parotid glands secrete much of the saliva which potentially interferes with dental treatment. Another feature of the appliance is that it takes advantage of dependent drainage of saliva when the patient is in the recumbent position, which is the position which modern dentistry is performed. This action of gravity aids in the device's effectiveness in treatment. With the absorbent rolls thus strategically positioned and bordering the work site, fluids which would interfere with the dentist's ability to complete the dental procedure are absorbed and eliminated. In addition, the appliance and rolls serve to retract tissues on either side of the work site such as the cheek or tongue, thus further facilitating the dentist or hygienist's completion of the dental work.

In addition to the basic description of the preferred embodiment described above, common alternative configurations departing slightly from the above design, but wholly within the spirit and scope of the dental appliance described above are as follows: Complementary mirror image absorbent roll holders that include a curvature of the metal members previously described as the rectangular projections of metal, including a curvature of the members along with a concurrent curvature of the associated narrow diameter shafts to conform to the natural curvature of an arch or quadrant of teeth is described. This allows a device to be positioned more to the front of the mouth. Also, a configuration allowing for only one absorbent roll to be positioned as needed is described. It is the intent of the inventor to describe not one, but a series of dental appliances all having design characteristics within the spirit and scope of the preferred embodiment as described herein that will be of benefit to dentists universally in the practice of dentistry.

The absorbent roll holder that is subject of this patent accommodates a polymer roll that has a hollow cylindrical sheath plastic that slides onto the metal shaft of the dental appliance engages a plastic locking mechanism composed of an enlarged spherical diameter of the shaft near the clasp arms to lock the cylindrical absorbent roll in place. The material external to the hollow plastic shaft is a starch absorbent polymer of a starch graft copolymer product derived from corn starch and acrylonitrile that was developed by the United States Department of Agricultural Research. Chemically, the polymer is a grafted polymer of starch and potassium acrylate, the technical name for which is starch-g-poly (starch-co-potassium acrylate). The outer shell of the cylindrical absorbent rolls is composed of an inner wrapper that has longitudinal folds which create a segmented wedge design. This is paralleled by a fine cotton mesh with a releasing cross-linked stitching cloth that allows liquids to be absorbed easily, but also allows the absorbent roll to expand significantly as liquids become absorbed within the polymer's chemical structure. This description of the absorbent roll is the preferred embodiment of the roll, but a simpler version of the absorbent roll with a simpler design of a locking mechanism, the same polymer throughout the interior, and with the external shell of an inner absorbent layer and an outer cotton mesh folded longitudinally to form a segmented wedge design is also presented as a cost-effective alternative is described. This absorbent roll would slide onto the shaft with a piercing action of a rubber or plastic diaphragm by the small diameter metal shaft and the spherical enlargement of the roll holder.

DESCRIPTION OF A PREFERRED EMBODIMENT

Figure 1:
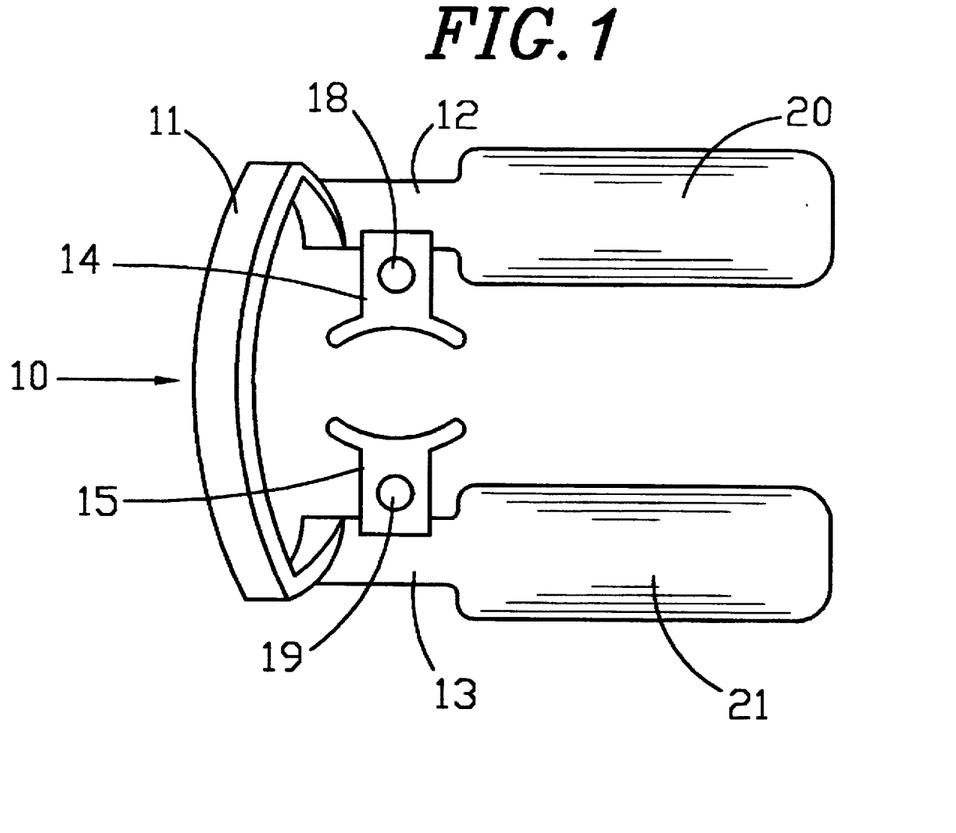
FIG. 1 is a top view of the dental appliance showing the body of the appliance, the clasp arms, clasps, and the rectangular metal projections.

Illustrated in FIG. 1, generally at 10 is the absorbent roll holder which is a symmetrical dental appliance for isolating various portions of the oral cavity and maintaining a dry field of operation by holding two absorbent rolls parallel to and adjacent to the teeth or tissues to be worked on. The dental appliance 10 includes a pair of arm members, 12, 13, which are operative arms that are linked to a transverse resilient metal arch member, 11, at the rear position of the appliance. The arms 12, 13, can be laterally displaced relative to one another by engaging two lumens, 18, 19, located on the clasp arms, 14, 15, extending transversely from each arm with a standard spreading forceps that dentists universally have in their armamentarium of dental instruments. When the forceps is engaged in each lumen 18, 19, and pressure is applied to the forceps by the dentist, the arms are displaced laterally away from one another in proportion to the amount of force applied by the operator. The dentist can then lower the dental appliance in its open or laterally displaced position over the clinically visible portion of the crown of a tooth. When the correct locations on the reciprocal convex surfaces of a tooth are located, the dentist then releases the tension on the dental appliance, thus allowing each of the reciprocal clasps, 16, 17, on the transverse clasp arms, 14, 15, of each operative arm, 12, 13, to engage the tooth. The tension of the resilient transverse metal arch member, 11, in its open position, then transmits a reciprocal force to each clasp, 16, 17, through the clasp arms, 14, 15, on each of the operative reciprocal arms, 12, 13. This reciprocal tension then holds the dental appliance in place in the mouth.

Figure 2:
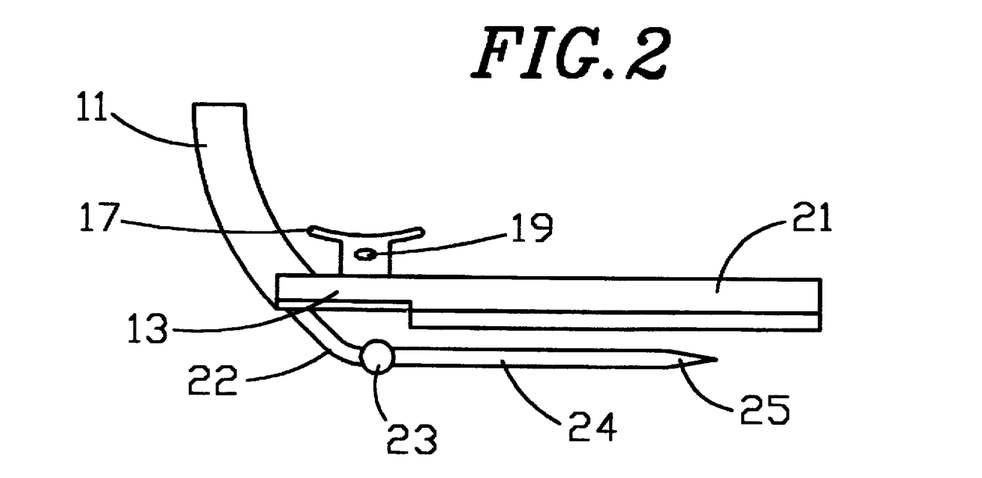
FIG. 2 is side view of the dental appliance showing the body of the appliance, the clasp arms, rectangular projection, and the narrow diameter metal shaft with a sperical enlargement.
Figure 3:
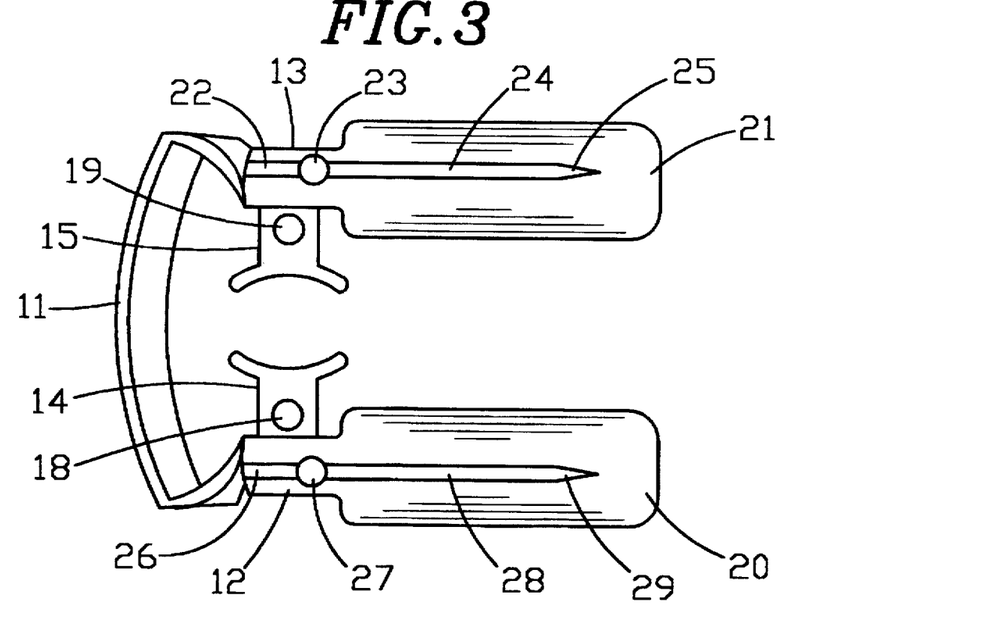
FIG. 3 is a bottom view of the dental appliance showing the body of the appliance, the clasp arms, the rectangular projection, and the narrow diameter metal shaft with a sperical enlargement.
Figure 4:
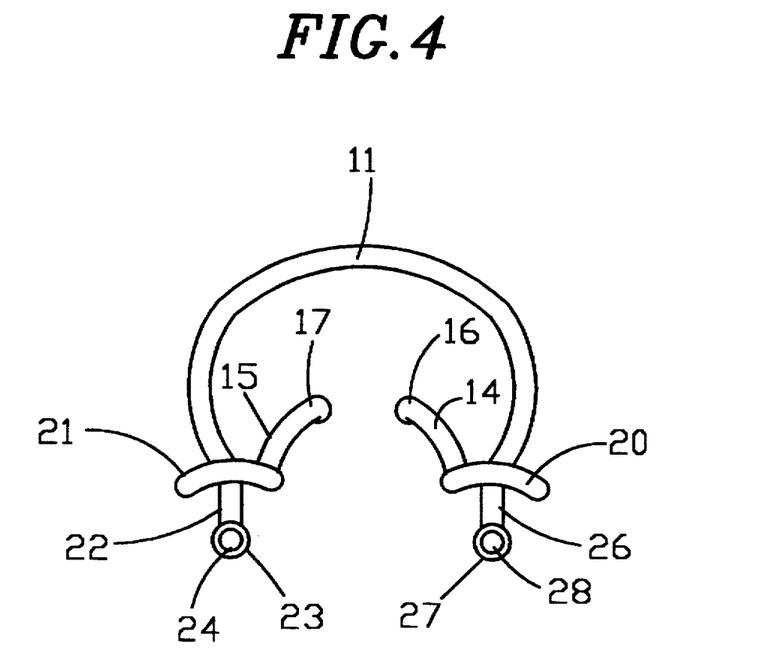
FIG. 4 is a front end view showing all structures in an front end orientation.

The end portions of each operative arm, 12, 13, located at the front end of the absorbent roll holder, as shown in FIG. 1 and in profile in FIG. 2, are away from the resilient transverse metal arch, 11, and consist of the operative ends of the dental appliance. Each consists of a rectangular projection of metal, 20, 21, curved convexly about an axis coincidental to the narrow metal shaft, 24, where it extends in a direction parallel to the longitudinal axis of each rectangular metal projection from the back to the front of the dental appliance. Extending downward and forward from each arm 12, 13, at the rear end of the dental appliance near the linkage of each arm with the resilient transverse metal member, 11, is a small diameter cylindrical metal shaft, 22, 26, attached to the appliance at the back end, then traveling generally in a direction from back to front, 24, 28, and in line with the longitudinal axis of each arm, 12, 13, to end with a conical point, 25, 29, below and at the proximity of the front end of each rectangular projection of metal, 20, 21. Both shafts can best be seen in FIG. 3, a bottom view, although FIG. 2 shows one of the shafts, 24, in profile. Located on both shafts of metal, at approximately below the front border of each clasp arm, 14, 15, is a spherical enlargement of metal, 23, 27. These spherical enlargements of metal engage the locking mechanism 29, of the safety-locking absorbent rolls when they are fully engaged with both shafts, 24, 28, of the absorbent roll holder.

Figure 5:
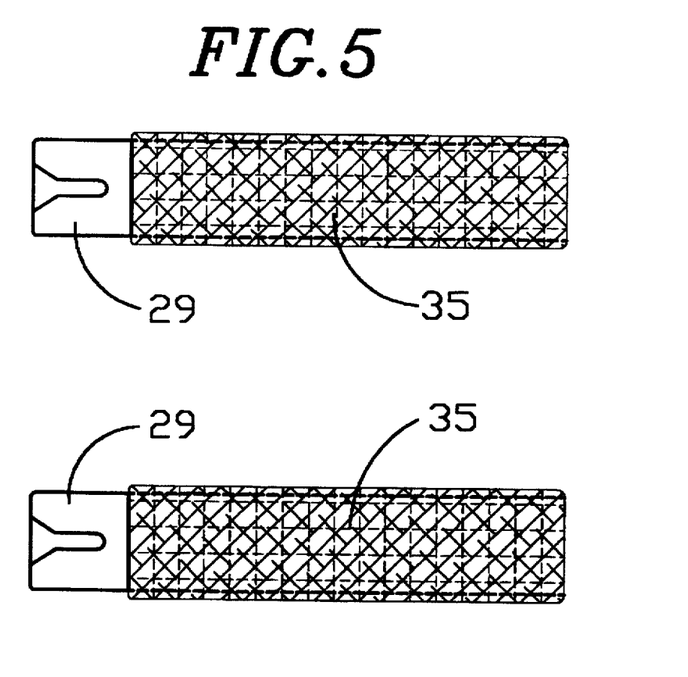
FIG. 5 shows two safety-locking absorbent rolls with a demonstration of the direction that each would be directed to place them on the dental appliance in relation to FIG. 1.
Figure 6:
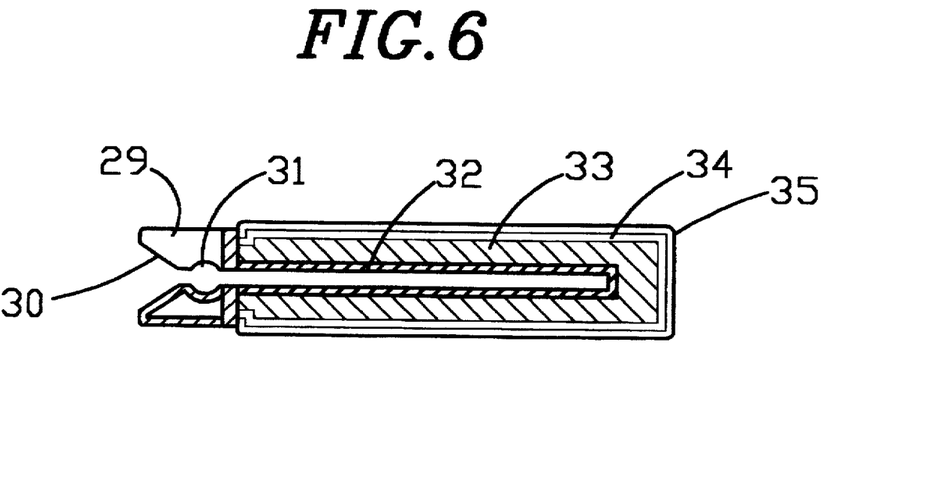
FIG. 6 shows a cross section of the safety-locking absorbent roll with its plastic shaft, the inclined plane and concave depression of the plastic members of the locking device, the polymer layer, inner wrapper, and cotton sheath.

FIG. 5 shows two safety-lock polymer absorbent rolls from a side view, with their longitudinal axes lined up to show the direction that these rolls are pushed along the metal shafts, 24, 28, of the absorbent roll holder in FIG. 1 for them to engage fully in their operative position. FIG. 6 is a cross sectional view of a safety-locking polymer absorbent roll. In this view, a hollow, flexible plastic cylindrical sheath, 32, with a plastic locking mechanism, 29, on the absorbent roll, which engages the narrow diameter metal shafts, 24, 28, and the spherical enlargements of metal, 23, 27, respectively on the absorbent roll holder. The cross sectional view of the safety-locking absorbent roll is shown in the proper relationship to FIG. 2, the side view of the dental appliance to demonstrate the direction in which the absorbent roll would be pushed with finger pressure to engage the small diameter cylindrical shaft, 24, and the spherical enlargement 23, as shown in this profile view to lock the absorbent roll in its operative position.

The safety-locking mechanism consists of a cylindrical plastic complex, 29, that is elastically deformed outward by the spherical enlargement as it pushes longitudinally against the inclined plane, 30, of each plastic member of the cylindrical plastic complex, but snaps back into its original position after sliding past the height of curvature of the metal sphere, 23, 27. The absorbent roll is then held in place by the reciprocal tension of the stressed plastic members of the locking mechanism. The concave inner surface, 31, of these plastic members thus engage the metal spherical portion of the shafts, holding the absorbent roll on the shaft and preventing it from sliding off. The operator can remove the absorbent rolls in much the same manner, by pulling longitudinally on the roll but in the opposite direction, thus expanding the plastic members within their elastic limit again by deforming them outward until the height of curvature is past and the members release the spherical enlargement and the roll slides off of the shaft.

The layer of material, 33, external to the plastic shaft, 32, in contact with it, but within the confines of the inner wrapper, 34, and the external cotton mesh covering 35, is a starch absorbent polymer of a starch graft copolymer product derived from corn starch and acrylonitrile that was developed by the United States Department of Agricultural Research. Chemically, the polymer is a grafted polymer of starch and potassium acrylate, the technical name for which is starch-g-poly (starch-co-potassium acrylate). This substance has been reported to have an absorptive capacity of as much as 2500 times its own weight in liquids. One of the characteristics of the polymer is that it expands significantly as it absorbs fluids. The outer coverings, then are designed to compensate for this need. The inner wrapper, 34, is folded longitudinally to form a segmented wedge design which allows a surplus of material which can contribute to a greater circumference as the diameter of the roll increases. The cotton sheath 35, forming the outer surface of the absorbent roll also allows the polymer to expand in the same manner as the roll becomes saturated with fluids during the course of dental treatment.

Figure 7:
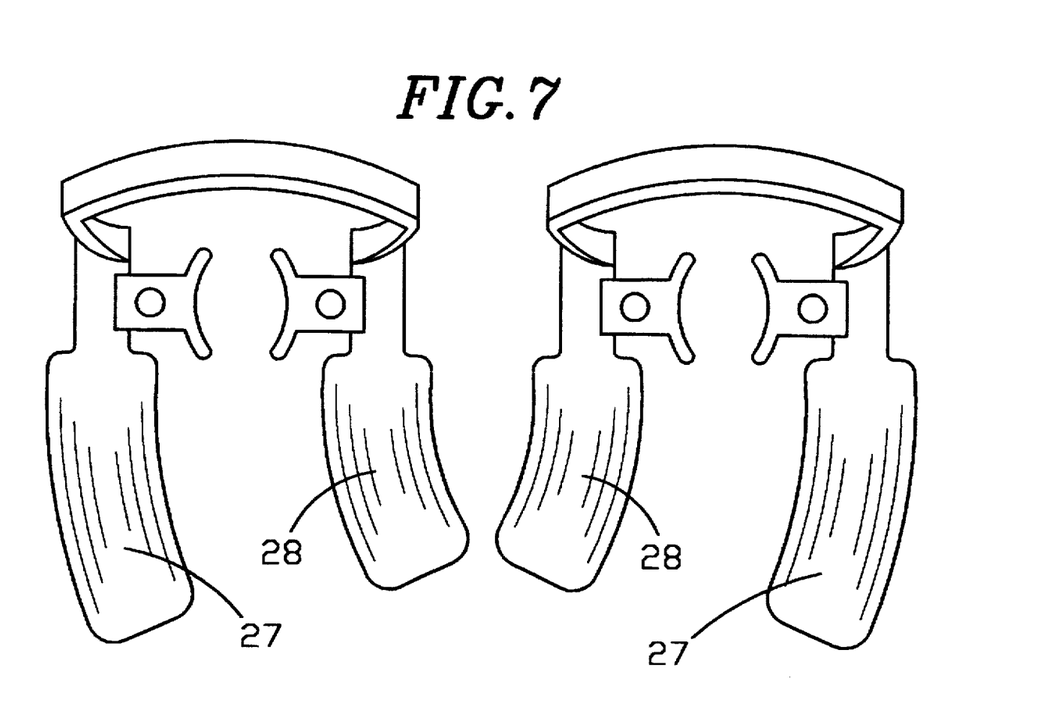
FIG. 7 and FIG. 8 show alternative configurations of the dental appliance; a set of two mirror-image curved models, FIG. 7; and an appliance with a single absorbent roll capacity, FIG. 8.

FIG. 7 shows a common alternative configuration of the preferred embodiment of the absorbent roll holder. It shows two complementary mirror image configurations of the appliance that allow a curvature of the member previously described as the rectangular projection of metal, 20, 21, but curved in such a manner as to follow the anatomical curvature of a quadrant of teeth. These two members are composed of an outer member, 27, a curvature that would follow the external curvature of an arch of teeth, allowing an absorbent roll to be positioned external to that arch, and an inner member, 28, having a curvature that would follow the inner curvature of an arch of teeth, allowing an absorbent roll to be positioned adjacent to the inner curvature of an arch of teeth. The associated small diameter metal shafts, 24, 28, also follow the same curvatures. This configuration of complementary appliances allows a more forward placement of the device in circumstances which procedures are planned for teeth further forward in the patient's mouth.

Figure 9:
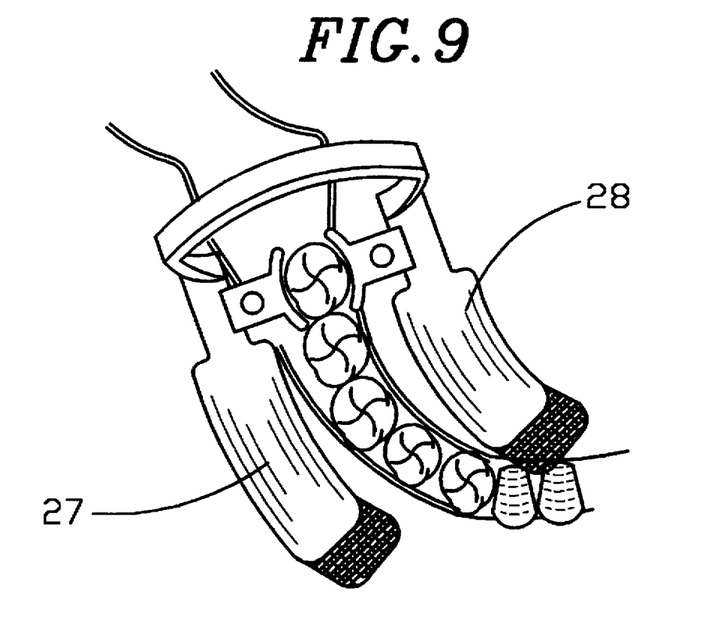
FIG. 9 shows a top view of the absorbent roll holder appliance and absorbent polymer rolls in operative position in the mandible (lower jaw) of a patient.

FIG. 9 shows a top view of an absorbent roll holder in an operative position in a patient's mouth with two absorbent rolls in place and flexed in a manner consistent with the curvature of the long axis of both of these members.

Figure 10:
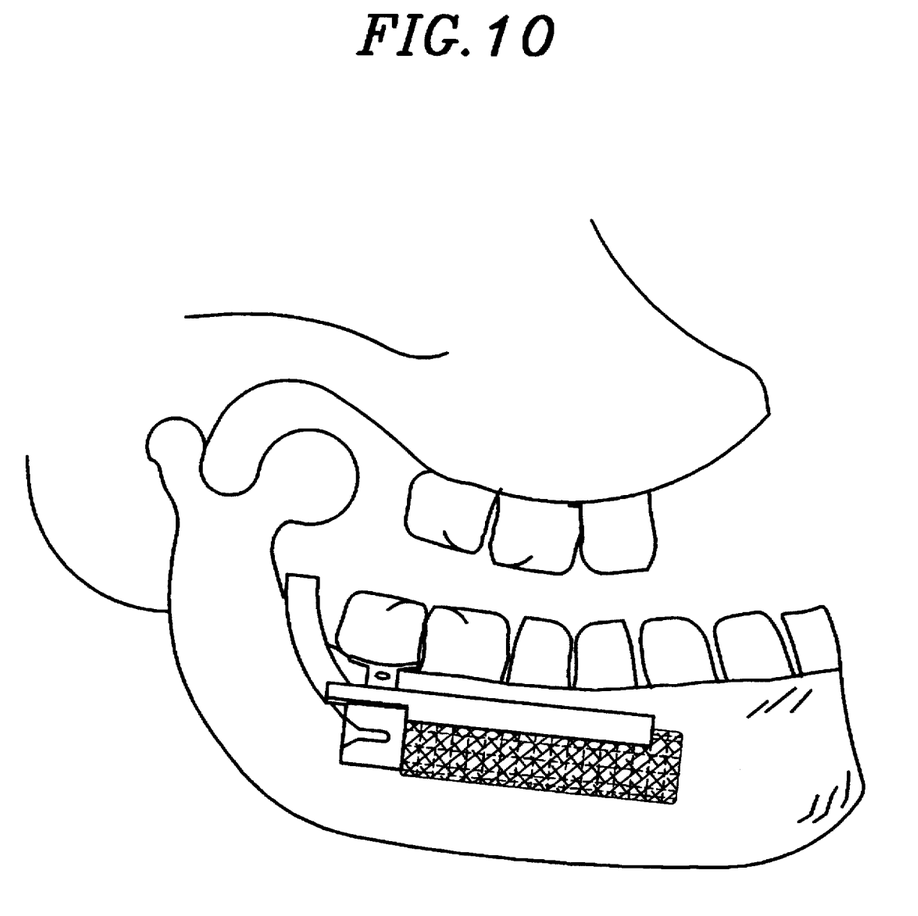
FIG. 10 shows a side view of the absorbent roll holder and an absorbent polymer roll in an operative position in the mandible (lower jaw) of a patient.

FIG. 10 shows a side view of this same absorbent roll holder with absorbent rolls in an operative position in a patient's mouth.

Figure 8:
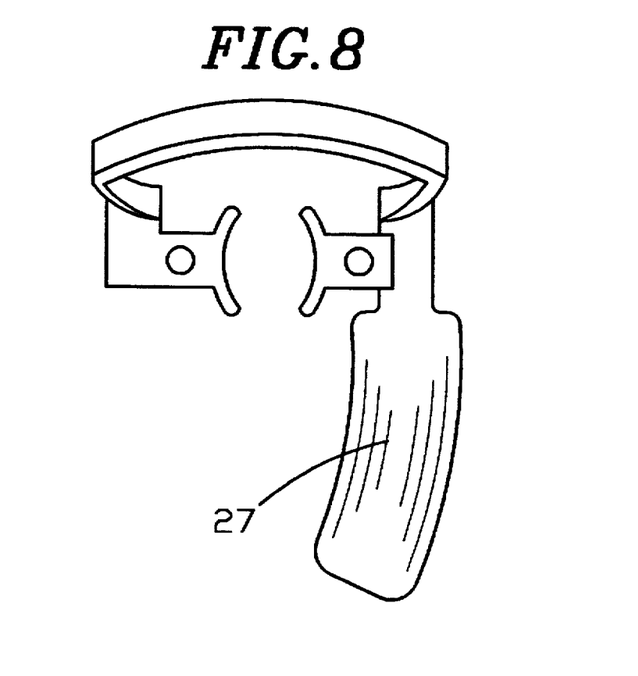
Figure 11:
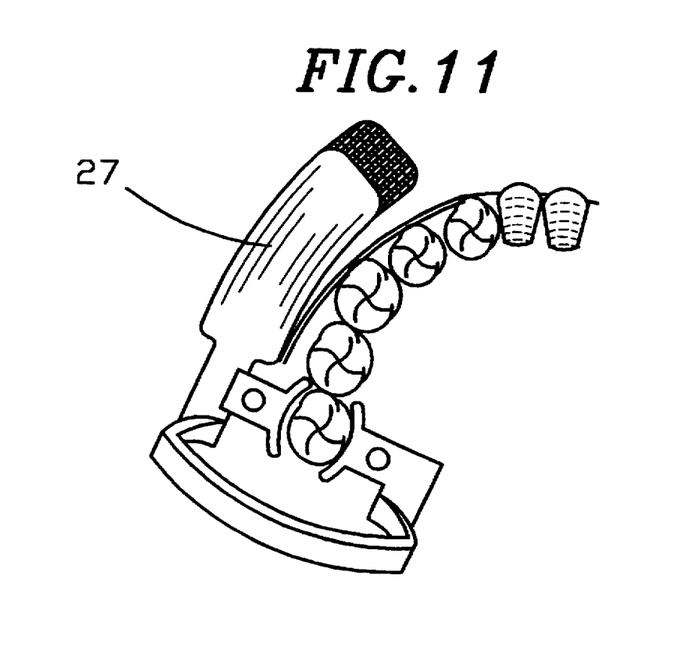
FIG. 11 shows a top view of the absorbent roll holder appliance and absorbent polymer rolls in an operative position in the maxilla (upper jaw) of a patient.
Figure 12:
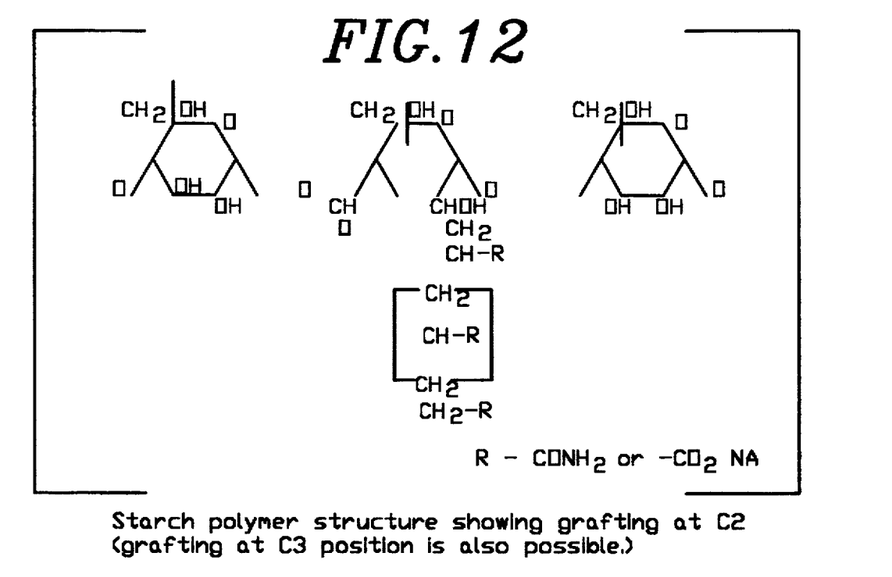
FIG. 12 is the chemical formula of the polymer.
Figure 13:
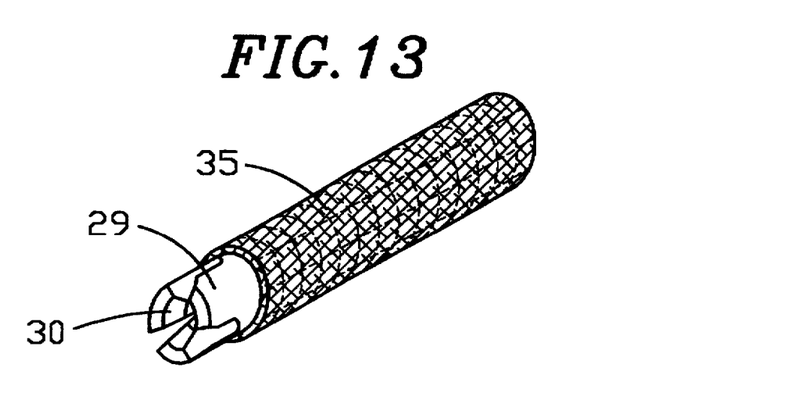
FIG. 13 is a perspective view of an absorbent polymer roll with a cylindrical locking mechansim in the foreground.
Figure 14:
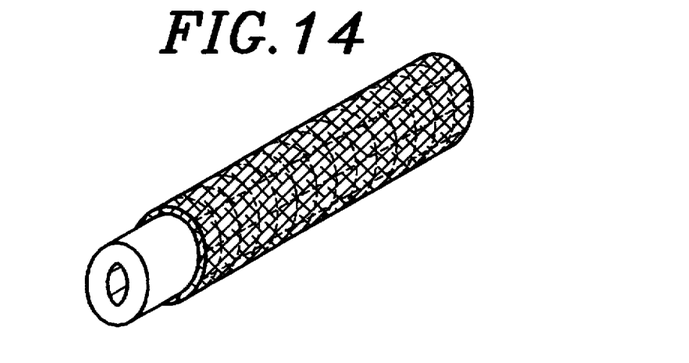
FIG. 14 is a perspective view of an alternative roll.

Another common configuration of the preferred embodiment of the absorbent roll holder series is illustrated in FIG. 8, an appliance which has a member that conforms to the outer radius of an arch of teeth, 27, but does not have an inner member which would position an absorbent roll adjacent to an inner diameter of a radius of teeth. This appliance would be appropriate in circumstances which the focus of a procedure was on the outer surfaces of teeth. The appliance is shown engaged in its operative position in a patient's mouth in FIG. 11. This appliance would be produced along with a mirror-image complementary appliance. Another variation, one which has only an inner member is planned.

Use of the absorbent polymer roll holder must be accompanied by good clinical technique, which relies on the use of dental floss to be secured to the appliance before insertion into the mouth for prevention of swallowing or aspiration if the appliance becomes dislodged. The appliance should always be placed with the free ends of the shafts pointing in an anterior direction to prevent the rolls from being swallowed or aspirated if dislodged during a procedure.

I claim:

1. A dental instrument for positioning and retaining one or more absorbent rolls in the oral cavity of a patient and for isolating areas of the oral cavity generally, comprising:
   (a) an inner arm member and an outer arm member, each of which has a first free end portion and a second, opposite end portion;
   (b) a resilient transverse arch member interconnecting said inner and outer arm members at said second end portions;

(c) opposing clasp means operatively associated with each of said arm members for engaging opposing inner and outer surfaces of a tooth, said opposing clasp means being biased to engage said tooth by said transverse arch member;

(d) means on each of said clasp means for engagement and separation by a dental forceps;

(e) an absorbent roll including an absorbent polymer; and (f) means on each of said arm members for retaining an absorbent roll in position in the oral cavity.

2. A dental instrument as defined in claim 1, wherein said retaining means on each of said arm members includes a pointed tip on said free end portion of each of said arm members.

3. A dental instrument as defined in claim 2, further comprising an elastic membrane covering an end portion of said absorbent roll, which elastic membrane is pierced by said pointed tip upon insertion of an arm member into said absorbent roll and which serves to retain said absorbent roll on an arm member during a dental procedure.

4. A dental instrument as defined in claim 2, further comprising strengthening means on an end portion of said absorbent roll for assisting in the insertion of said arm member into said roll.

5. A dental instrument as defined in claim 1, further comprising locking means on each of said arm members near said second, opposite end portions thereof for releasably holding said absorbent roll on said arm members, and wherein said locking means includes a substantially spherical protrusion on each said arm member, and means operatively associated with said absorbent roll for releasably engaging said spherical protrusion.

6. A roll holder as defined in claim 1, wherein said polymer includes the starch absorbent polymer starch-g-poly (starch-co-potassium acrylate).

7. A dental instrument as defined in claim 1, wherein said arm members are positioned below said clasp means so that when said roll holder is in its operative position supported on a tooth, said absorbent roll is positioned in the region of accumulation of saliva adjacent the isolated areas of the oral cavity, and wherein said roll is adapted to be positioned adjacent openings of the submanidbular ducts, the sublingual ducts, or the parotid gland.

8. A dental instrument as defined in claim 1, wherein said absorbent rolls are positioned in the oral cavity in contact with the lowest points of the oral cavity of a recumbent patient during a dental procedure.

9. A dental instrument as defined in claim 1, wherein said roll includes an absorbent cotton roll.

10. A dental instrument as defined in claim 1, further comprising shield means spaced above each of said arm members for preventing expansion of said absorbent (rolls) into said isolated areas of the oral cavity, and wherein said absorbent (rolls are) roll is substantially cylindrical and said shield means are curved upwardly to accommodate the cylindrical absorbent (rolls) roll.

11. A dental instrument for positioning and retaining one or more saliva ejectors in the oral cavity of a patient and for isolating areas of the oral cavity generally, comprising:

(a) an inner arm member and an outer arm member, each of which has a first free end portion and a second, opposite end portion;

(b) a resilient transverse arch member interconnecting said inner and outer arm members at said second end portions;

(c) opposing clasp means operatively associated with each of said arm members for engaging opposing inner and outer surfaces of a tooth, said opposing clasp means being biased to engage said tooth by said transverse arch member;

(d) means on each of said clasp means for engagement and separation by a dental forceps;

(e) means on each of said arm members for retaining a saliva ejector in position in the oral cavity; and (f) further comprising locking means on at least one of said arm members near said second, opposite end portion thereof for releasably holding said saliva ejector on said arm member, and wherein said locking means includes a substantially spherical protrusion on said arm member, a tubular sheath on the longitudinal axis of said saliva ejector, and means operatively associated with said tube for releasably engaging said spherical protrusion.

* * * * *